United States Patent
Rafkin

(10) Patent No.: US 6,844,014 B1
(45) Date of Patent: Jan. 18, 2005

(54) HERBAL HEALING LOTION FOR VETERINARY USE

(76) Inventor: Stephen Rafkin, 62 Alpine Dr., Woodridge, NY (US) 12789

( * ) Notice: Subject to any disclaimer, the term of this patent is extended or adjusted under 35 U.S.C. 154(b) by 16 days.

(21) Appl. No.: 10/200,542

(22) Filed: Jul. 22, 2002

(51) Int. Cl.[7] .................. A61K 35/78; A61K 31/74; A61K 39/395
(52) U.S. Cl. .............. 424/725; 424/730; 424/744; 424/78.02; 424/78.03; 424/157.1
(58) Field of Search ............... 514/863, 864, 514/2; 424/744, 157.1, 725, 730, 78.02, 78.03, 78.05, 78.06, 642

(56) References Cited

U.S. PATENT DOCUMENTS

| | | | |
|---|---|---|---|
| 4,268,526 A | | 5/1981 | Vargas et al. |
| 4,569,839 A | | 2/1986 | Grollier et al. |
| 4,822,595 A | | 4/1989 | Corliss et al. |
| 4,837,019 A | | 6/1989 | Georgalas et al. |
| 4,917,891 A | | 4/1990 | Kaufmann et al. |
| 5,165,932 A | | 11/1992 | Horvath |
| 5,260,292 A | | 11/1993 | Robinson et al. |
| 5,368,779 A | | 11/1994 | Snethen |
| 5,433,954 A | * | 7/1995 | Smith et al. ............ 424/646 |
| 5,466,680 A | | 11/1995 | Rudy |
| 5,558,914 A | * | 9/1996 | Cohen et al. ............ 424/59 |
| 5,693,327 A | | 12/1997 | Shah |
| 5,738,863 A | * | 4/1998 | Sackin et al. ............ 424/405 |
| 5,750,149 A | * | 5/1998 | Gobbi ............ 424/535 |
| 5,776,477 A | | 7/1998 | Ryder |
| 5,863,546 A | | 1/1999 | Swinehart |
| 5,871,756 A | * | 2/1999 | Jeffcoat et al. ............ 424/401 |
| 5,922,313 A | | 7/1999 | Steward et al. |
| 5,922,331 A | | 7/1999 | Mausner |
| 5,980,870 A | | 11/1999 | Baik et al. |
| 6,099,866 A | | 8/2000 | Slimak |
| 6,103,246 A | | 8/2000 | Tisdale et al. |
| 6,180,609 B1 | | 1/2001 | Gefter et al. |
| 6,200,570 B1 | | 3/2001 | Diwan et al. |
| 6,200,594 B1 | | 3/2001 | Ernest et al. |

FOREIGN PATENT DOCUMENTS

| | | | |
|---|---|---|---|
| CA | 2163854 | | 6/1996 |
| DE | 4227806 | | 2/1993 |
| JP | 11199461 | | 7/1999 |
| JP | 11-199461 | | 7/1999 |
| RO | 1106779 B1 | * | 5/1996 |
| WO | WO89/09049 | | 5/1989 |

OTHER PUBLICATIONS

Drug Topics (Mar. 6, 2000), 144(5): 130. Lake Consumer Products.*

Lust, John B., N.D., D.B.M. The Herb Book (1974), Benedict Lust Publications, New York, NY, p. 402.*

* cited by examiner

Primary Examiner—Michele C. Flood
(74) Attorney, Agent, or Firm—Michael I. Kroll

(57) ABSTRACT

A herbal healing lotion in the form of a topical composition for relieving dermatological skin conditions encountered by animals. The composition is topically applied to an affected area of skin of the animal. The topical composition contains a vehicle for distributing the active ingredients to the affected skin. The vehicle is comprised of water, carboxymethylcellulose, and colostrum which allows for the active ingredients to be received by the skin on surface and deep tissue layers. The herbal healing lotion contains no steroid or antibiotic component thereby preventing immunosuppression generally associated therewith. The herbal healing lotion combines natural ingredients in a topical composition to successfully treat dermatological conditions previously held as untreatable.

11 Claims, 1 Drawing Sheet

HERBAL HEALING LOTION FOR VETERINARY USE

BACKGROUND OF THE INVENTION

1. Field of the Invention

Figure 1:
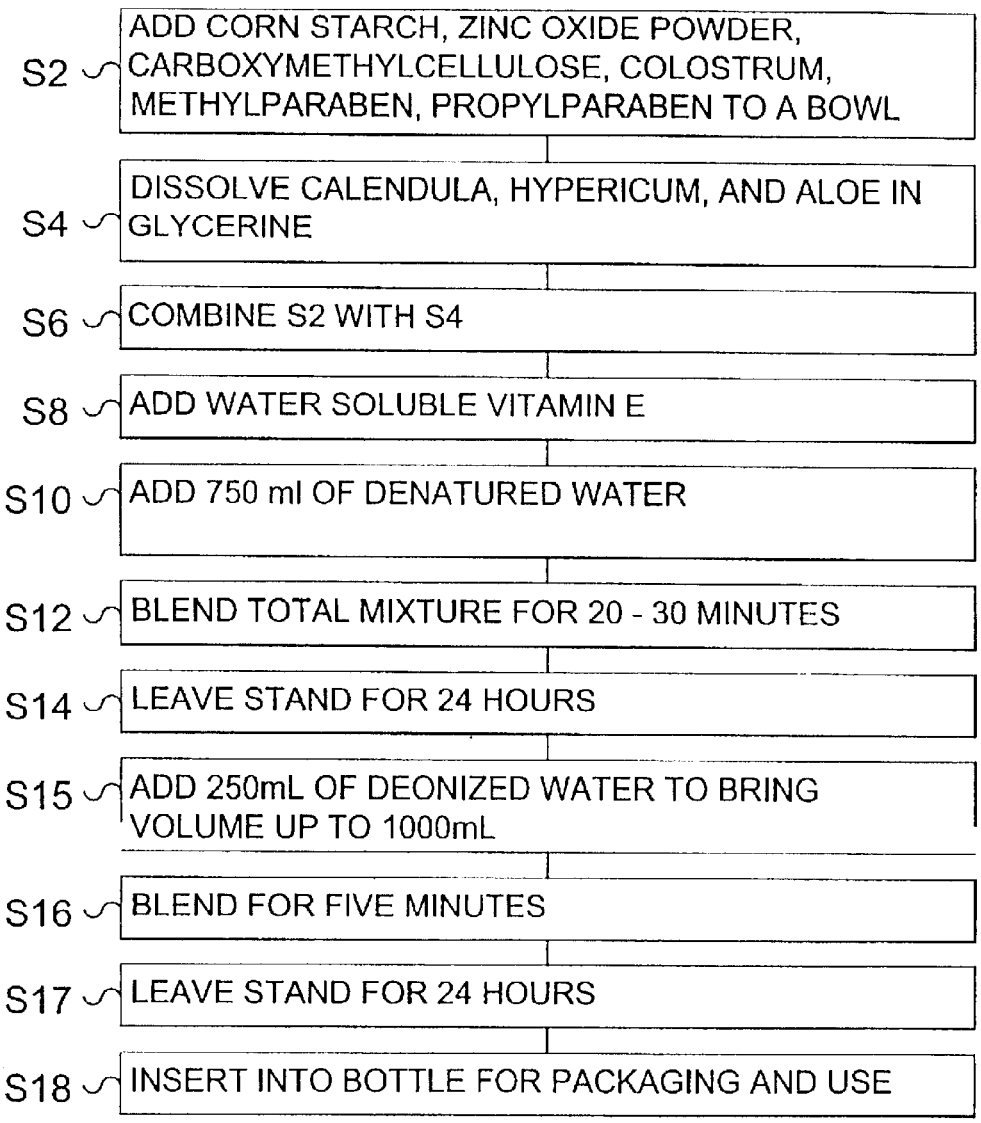

The present invention relates to (non-prescription) topical compositions for veterinary use and, more specifically, to a non-antibiotic and non-steroid topical composition formed from a carboxymethylcellose water miscible vehicle combined with colostrum for treatment and cure of varying dermatological conditions encountered by animals.

2. Description of the Prior Art

Animals suffer from varying dermatological conditions that cause irritation and distress. Such dermatological conditions include Otitis Externa, Hot Spots, abrasions, burns, dermatitis, poison ivy, hives, insect bites, and lick granuloma. Previous methods for caring for such conditions used steroidal methods that tend to destroy the health of animals because of the steroids immunosuppresive activity.

It is thus desirable to provide an herbal healing lotion using pure, natural ingredients to treat and cure these conditions. It is further desirable to provide an herbal healing lotion which does not include steroids. It is still further desirable to provide an herbal healing lotion which does not destroy the health of the animals being treated due to the immunosuppresive activity of the ingredients.

SUMMARY OF THE PRESENT INVENTION

The present invention relates to (non-prescription) topical compositions for veterinary use and, more specifically, to a non-antibiotic and non-steroid topical composition formed from a carboxymethylcellose water miscible vehicle combined with colostrum for treatment and cure of varying dermatological conditions encountered by animals.

It is therefore a primary object of the present invention to provide a composition for topical application for the relief of distressful dermatological conditions suffered by animals that overcomes the shortcomings of the prior art.

It is a further object of the present invention to provide a composition for topical application for the relief of distressful dermatological conditions suffered by animals that is able to relieve discomfort associated with the skin conditions without the use of a steroid and/or antibiotics.

It is a further object of the present invention to provide a composition for topical application for the relief of distressful dermatological conditions suffered by animals including herbs, minerals, vitamins, natural vegetable products and colostrum.

It is yet a further object of the present invention to provide a topical composition for topical application for the relief of distressful dermatological conditions suffered by animals that is able to treat deep layers of skin, as well as surface skin.

It is still a further object of the present invention to provide a topical composition for topical application for the relief of distressful dermatological conditions suffered by animals that will not suppress the immune system of the treated animal if accidentally ingested.

It is a further object of the present invention to provide a topical composition for topical application for the relief of distressful dermatological conditions suffered by animals that deters the animal from actively licking the treated skin.

It is another object of the present invention to provide a topical composition for topical application for the relief of distressful dermatological conditions suffered by animals that can be easily removed from the area to which it was applied using warm water.

It is a further object of the present invention to provide a topical composition for topical application for the relief of distressful dermatological conditions suffered by animals that provides a protective layer around the treated skin that insulates the affected area from external irritants such as insect bites and wind and sun burns.

It is still a further object of the present invention is to provide a herbal healing topical composition for topical application for the relief of distressful dermatological conditions suffered by animals and method of production therefore that is economical in cost to manufacture.

It is still a further object of the present invention is to provide a herbal healing topical composition for topical application for the relief of distressful dermatological conditions suffered by animals and method of production therefore that is simple and easy to use.

To the accomplishment of the above and related objects, this invention may be embodied in the form illustrated in the disclosure, attention being called to the fact, however, that the items mentioned in the disclosure are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a flow diagram illustrating the method of preparing the composition for topical application for the relief of distressful dermatological conditions suffered by animals of the present invention.

DETAILED DESCRIPTION OF THE PRESENT INVENTION

In the past animals have suffered discomfort associated with variable dermatological conditions that were treated by veterinarians with mixed results. Examples of such dermatological conditions include Otitis Externa, hot spots, abrasions, burns, dermatitis, poison ivy, hives, insect bites, and lick granuloma. Generally the treatment of these conditions consisted of prescription antibiotics that may contain a steroid component. The result of this method of treatment is potential immunosuppression if the antibiotic with a steroid component was licked off the affected area. Also, another consequence of the previous treatment methods is the development of "super bacteria" if the antibiotics were prescribed incorrectly or haphazardly.

The herbal healing lotion of the present invention uses carboxymethylcellulose as a vehicle to deliver the active ingredients of the herbal healing lotion to the deepest layers of skin. The carboxymethylcellulose is combined with de-ionized water and colostrum to complete the vehicle.

This combination of caboxymethylcellulose with water and colostrum as a vehicle to treat dermatological conditions has never been employed. Typically colostrum when mixed with water creates an unstable substance. This mixture of colostrum and water posed problems when intended for external use such as a short shelf life and a requirement of refrigeration. Further, when preservatives were added to the mixture of colostrum and water neither of the above mentioned problems were rectified. However, in the herbal healing lotion of the present invention, the problems previously identified have been solved by the addition of caboxymethylcellulose to the combination of water and colostrum. The colostrum in the herbal healing lotion does not require refrigeration and it has a long shelf life.

The use of a vehicle composed of carboxymethylcellulose, water, and colostrum provide advantages over previous methods of treatment. Firstly, because the components of the herbal healing lotion are water soluble, the vehicle allows for the active ingredients to reach the deepest layer of skin. Further, the makeup of the herbal healing lotion is such that it is completely water miscible. This allows for easy and quick removal of the herbal healing lotion with a small amount of warm water. Once removed, the area of skin on the animal is prepared for re-application of the herbal healing lotion.

Colostrum is an important part of the herbal healing lotion because of its natural healing abilities. Specifically, colostrum stimulates epithelial cell growth which accelerates the healing process. Colostrum is also used because of its infection fighting ability.

The invention is explained in greater detail below on the basis of examples which are not intended to restrict the scope of the invention in any way. The percentage amounts given are always based on weight, unless otherwise indicated. The preferred ranges of the composition for the topical composition for topical application for the relief of distressful dermatological conditions suffered by animals is as follows.

| Preferred Ranges for Topical Composition | |
| --- | --- |
| Corn Starch | 50–100 g |
| Zinc Oxide Powder | 50–100 g |
| Carboxymethylcellulose | 8–12 g |
| Colostrum (Bovine) | 10–15 g |
| Methylparaben | 1.67 g |
| Propylparaben | 0.2 g |
| Vitamin E (water soluble) | 40–60 ml |
| Calendula | 1.5–2 g |
| Hypericum | 1.5–2 g |
| Aloe | 1.5–2 g |
| Glycerine | 25 ml |

Deionized Water to bring volume up to 1000 ml.

A preferred embodiment for the topical composition for topical application for the relief of distressful dermatological conditions suffered by animals is as follows:

| Example 1 | |
| --- | --- |
| Corn Starch | 100 g |
| Zinc Oxide Powder | 100 g |
| Carboxymethylcellulose | 10 g |
| Colostrum (Bovine) | 13.4 g |
| Methylparaben | 1.67 g |
| Propylparaben | 0.2 g |
| Vitamin E (water soluble) | 50 ml |
| Calendula | 1.83 g |
| Hypericum | 1.83 g |
| Aloe | 1.83 g |
| Glycerine | 25 ml |

Deionized Water to bring volume up to 1000 ml.

In addition to or in substitution of Calendula, Hypericum, and Aloe, the topical composition for treating dermatological conditions suffered by animals can contain at least Tea Tree Oil and White Willow Bark Extract. The Tea Tree Oil and White Willow Bark Extract are added in an amount substantially 1.83 g.

The method of producing the topical composition for topical application for the relief of distressful dermatological conditions suffered by animals will now be described with specific reference to FIG. 1. The corn starch, zinc oxide powder, carboxymethylcellulose, colostrum, methylparaben and propylparaben are placed in a bowl as discussed in step S2. The above mentioned ingredients are preferably in powder form. The calendula, hypericum, and aloe are then dissolved in the glycerine as stated in step S4. The glycerine and dissolved nutrients, i.e. calendula, hypericum, and aloe, are then added to the powder as described in step S6. Water soluble Vitamin E is then added to the combination as described in step S8. After the addition of Vitamin E, an amount substantially equivalent to 75% of the total amount of deionized water of 1000 ml is added to bring the volume of the mixture up to 750 ml as discussed in step S10.

The mixture is then blended for a total of twenty-five minutes as stated in step S12. Upon completion of steps S10 and S12, the volume of the mixture increases and the mixture exhibits a bubbling and foaming effect. The blended mixture is then left to settle for twenty-four hours as described in step S14. The settling step S14 allows for the reaction to slow down. Thereafter, an additional 250 ml of deionized water is added to the mixture as discussed in step S15. Once the twenty-four hour settling period has expired and the additional 250 ml of deionized water is added, the mixture is again blended for a total of five minutes as discussed in step S16. Once blended for a second time, the mixture is then left to settle for an additional 24 hours as stated in step S17. The herbal healing lotion is now ready for bottling as stated in step S18.

Case Studies

The efficacy associated with the herbal healing lotion of the present invention is best described through case studies. The following case studies are illustrative and in no way limit the application of the herbal healing lotion but are provided solely for purposes of example to show the effectiveness of the present invention.

Case 1: "Nanook"

Nanook, is a thirteen year old female husky that, prior to treatment, had interdigital dermatitis with an adenoma. Further examination revealed moist exudative skin inflammation between the toes of the (Right or Left) front paw and a skin growth. The skin growth was determined to result from licking of the area by the animal.

The treatment prescribed was to shave the fur around the lesion and soak the paw with a dilute betadyne disinfectant at the time of the first office visit. Further, the herbal healing lotion was prescribed for application in both the morning and evening. A re-examination was scheduled for two weeks later.

Upon re-examination, the paw exhibited signs of healing. The swelling of the adenoma has decreased. The owner farther reported that Nanook no longer licks his paw.

Case 2: "Tess"

Tess, is a nine year old Shitzu which, prior to treatment, had crusted itchy skin inflammation of the trunk. There were multiple raised lesions with a diameter of 1–2" where hair had been licked off. The lesions were red in color.

The treatment consisted of clipping and disinfecting the areas around the lesions. A homeopathic prescription along with the herbal healing lotion was dispensed to the owner. The herbal healing lotion was to be rubbed into the lesions in the morning and evening. A reexamination was scheduled for three weeks later.

Upon re-examination, the lesions treated with the herbal healing lotion had healed. New lesions in other areas had formed determined to be because of the ineffectiveness of the homeopathic medicine. A new prescription was chosen and the new lesions were to be treated by application of the herbal healing lotion in the morning and evening.

Case 3: "Max"

Max, a five year old golden retriever which had hot spots at the base of his tail prior to treatment. Further examination revealed that flea infestation was the cause of the hot spots. Treatment consisted of institution of flea control measures, clipping and disinfecting the hot spots and application of the herbal healing lotion. The herbal healing lotion was to be applied to the hot spots in the morning and evening. Five days after initial office visit, the owner reported that the lesions were no longer itchy, there was no inflammation and the hair had began to grow back.

Case 4: "Sheba"

Sheba is a six year old black lab mix which, prior to treatment, had blisters on the paw pad and a skin junction that had been poorly controlled since its initial diagnosis approximately 3 years before the present office visit. The skin junction had previously been controlled with prescribed steroid and immunosuppressive medication.

The method of treatment consisted of weaning Sheba off of the immunosuppressive medication over a three month period while internal homeopathic medications and nutrients were used. The herbal healing lotion was to be applied to the skin blisters twice daily.

The owner reported that energy levels immediately increased, and while the skin blisters continued, the animal appeared to be more comfortable with continued application of the herbal healing lotion. The skin condition from which Sheba suffers is quite serious with no cure. The herbal healing lotion appeared to reduce suffering and keep the condition under control.

Case 5: "Patches"

Patches is a 2 year old cat which had a long, itchy, serpentine skin lesion on the abdomen prior to treatment. Prior to the office visit, the previous veterinarian treated the lesion with cortisone and panalog whereby no positive result was obtained.

A new treatment of a hypoallergenic home prepared diet with homeopathic oral medication was inistituted. Further, the herbal healing lotion was prescribed for application to the lesion three times a day for a period of two weeks.

Four days after the initial office visit where the herbal healing lotion was dispensed, the owner called to report that the itch associated with the lesion had disappeared. The re-examination after six weeks showed a faint scar of the lesion with most of the hair surrounding the area fully re-grown.

Case 6: "Nameless"

A nameless puppy with an unidentified age presented by a good samaritan exhibited hairless crusted ear flaps and elbows prior to treatment. Further examination revealed mange mites. The treatment consisted of a mild bath and pyrethrin dip repeated three times at one week intervals. The herbal healing lotion was also applied to the lesions between the bath and dip. The good samaritan reported that the itch had ceased after five days and at thirty days the owner reported uneventful healing.

Case 7: "Socks"

Socks is an eight week old kitten that had gray crusted hairless patches on the face and paws prior to treatment. An antifungal culture was performed on the lesions. While waiting for the results, the lesions were treated with herbal healing lotion. The results of the antifungal culture showed ringworm. A re-examination at a week showed some healing but the lesions were still active. An oral antifungal known as griseofulvin was added to the treatment regiment. The lesions were cured after five weeks of treatment comprised of the oral antifungal and the herbal healing lotion. This case demonstrates the need for internal along with external treatment of dermatological conditions.

Case 8: "Spike"

Spike is a nine month old male rottweiler which had a sparse coat of hair over his chin and neck prior to treatment. Further examination and tests revealed a hookworm intestinal infestation and a demodex mite hair follicle infestation.

Treatment consisted of improving the animals diet, along with prescription of homeopathic medicine and internal parasite control. The herbal healing lotion was also dispensed for application once daily to the neck and chin areas for a period of two weeks.

Upon a re-examination after two weeks, the fur on the chin and neck area of the animal showed a growth over fifty percent on the initially identified area. The herbal healing lotion was discontinued after the re-examination. A second re-examination at eight weeks showed no mites were present in a skin scraping. Thereafter the case was deemed cured.

Case 9: "Duke"

Duke is a 2 year old male retriever that exhibited ear discharge with malodor and an itch during the swimming season. The treatment consisted of a weekly ear cleaning and application of two drops of the herbal healing lotion to each ear canal. At the one month mark, the condition was under control.

Case 10: "Peanut"

Peanut is a five year old female exhibiting hives and crust around the anus and abdomen. The owner spotted the condition after Peanut had been seen lying on a freshly mowed lawn. The prescribed treatment was a burrows solution soak followed by twice daily application of the herbal healing lotion to the affected area around the anus and abdomen. The owner reported that after five days the condition was resolved.

From the above description it can be seen that the herbal healing lotion of the present invention is able to overcome the shortcomings of prior art devices by providing a topical composition composed of entirely natural ingredients and without the use of a steroid or antibiotic component for curing various dermatological conditions suffered by animals. The topical composition is able to relieve discomfort associated with the skin conditions without the use of a steroid and/or antibiotics and includes herbs, minerals, vitamins, natural vegetable products and colostrum. The topical composition is able to treat deep layers of skin, as well as surface skin while not suppressing the immune system of the treated animal if accidentally ingested and deterring the animal from actively licking the treated skin. The topical composition can be easily removed from the area to which it was applied using warm water and provides a protective layer around the treated skin that insulates the affected area from external irritants such as insect bites and wind and sun burns. Furthermore, the herbal healing lotion is economical in cost and provides a safe natural way to treat dermatological skin conditions previously considered untreatable.

Whereas the invention has been described herein with reference to the presently preferred pharmaceutical composition listed above, it should be understood that various changes may be made by one skilled in the art without departing from the disclosed inventive concepts particularly pointed out above and as claimed by me hereinafter.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A topical composition for relief of dermatological conditions encountered by animals comprising an effective amount of corn starch, zinc oxide powder, carboxymethylcellulose, colostrum, methylparaben, propylparaben, Calendula, Hypericum, Aloe, glycerine, water soluble vitamin E, and deionized water.

2. The topical composition as recited in claim 1, wherein the composition is in the form of a lotion.

3. The topical composition as recited in claim 1, wherein the corn starch is present in an amount ranging from substantially 50 grams to substantially 100 grams; the zinc oxide powder is present in an amount ranging from substantially 50 grams to substantially 100 grams; the carboxymethylcellulose is present in an amount ranging from substantially 8 grams to substantially 12 grams; the colostrum is present in an amount ranging from substantially 10 grams to substantially 15 grams; the methylparaben is present in an amount of 1.67 grams; the propylparaben is present in an amount of 0.2 grams; the water soluble vitamin E is present in an amount ranging from substantially 40 milliliters to substantially 60 milliliters, the Calendula is present in an amount ranging from substantially 1.5 grams to substantially 2.0 grams; the Hypericum is present in an amount ranging from substantially 1.5 grams to substantially 2.0 grams; the Aloe is present in an amount ranging from substantially 1.5 grams to substantially 2.0 grams; and the glycerine is present in an amount of 25 milliliters.

4. The topical composition as recited in claim 3, wherein the corn starch is present in an amount of 100 grams; the zinc oxide powder is present in an amount of 100 grams; the carboxymethylcellulose is present in an amount of 10 grams; the colostrum is present in an amount of 13.4 grams; the methylparaben is present in the amount of 1.67 grams; the propylparaben is present in the amount of 0.2 grams; an Calendula is present in the amount of 1.83 grams; the Hypericum is present in an amount of 1.83 grams; the Aloe is present in an amount of 1.83 grams; the glycerine is present in the amount of 25 milliliters; the water soluble vitamin E is present in an amount of 50 milliliters.

5. The topical composition as recited in claim 1, further comprising at least Tea Tree Oil and White Willow Bark Extract.

6. The topical composition as recited in claim 5, wherein the Tea Tree Oil is present in an amount ranging from 1.5–2.0 grams; and the White Willow Bark Extract is present in an amount ranging from 1.5–2.0 grams.

7. The topical composition as recited in claim 1, wherein the composition is water miscible thereby allowing easy removal with a small amount of water.

8. The topical composition as recited in claim 1, wherein the composition remains effective for the relief of dermatological conditions encountered by animals when stored at room temperatures.

9. The topical composition as recited in claim 1, wherein the composition forms a protective layer on the skin of the animal for protection from at least one of sun, wind, and licking by the animal.

10. The topical composition as recited in claim 1, wherein the composition allows for the deepest layers of skin to be treated.

11. A topical composition for relief of dermatological conditions encountered by animals consisting of an effective amount of corn starch, zinc oxide powder, carboxymethylcellulose, colostrum, methylparaben, propylparaben, calendula, hypericum, aloe, glycerine, water soluble vitamin E, and deionized water.

* * * * *